United States Patent [19]

Jakobson et al.

[11] Patent Number: 4,992,594

[45] Date of Patent: Feb. 12, 1991

[54] PROCESS FOR THE PREPARATION OF POLYGLYCEROLS

[75] Inventors: Gerald Jakobson; Werner Siemanowski, both of Rheinberg, Fed. Rep. of Germany

[73] Assignee: Deutsche Solvay-Werke GmbH, Solingen, Fed. Rep. of Germany

[21] Appl. No.: 460,380

[22] Filed: Jan. 3, 1990

[30] Foreign Application Priority Data

Jan. 3, 1989 [DE] Fed. Rep. of Germany ....... 3900059

[51] Int. Cl.$^5$ ............................................. C07C 41/03
[52] U.S. Cl. ................................... 568/680; 568/620; 568/679
[58] Field of Search ................... 568/620, 679, 680

[56] References Cited

U.S. PATENT DOCUMENTS 2,520,670  8/1950  Wittcoff et al. ..................... 260/615

Primary Examiner—Howard T. Mars
Attorney, Agent, or Firm—Foley & Lardner, Schwartz, Jeffery, Schwaab, Mack, Blumenthal & Evans

[57] ABSTRACT

A process is disclosed for the preparation of polyglycerols (containing more than 50% by weight of diglycerol) which have a low content of cyclic components, by reacting chlorohydrins. In this reaction α-monochlorohydrin and epichlorohydrin are reacted at temperatures of 20° to 120° C., preferably 50° C. to 100° C., in a molar ratio of epichlorohydrin to α-monochlorohydrin of 0.8:1 to 1:2.5 in the presence of acids or compounds having an acid reaction. A medium having an alkaline reaction, preferably an aqueous solution having an alkaline reaction, is added to the resulting unseparated reaction mixture, at a temperature of 50° C. to 120° C., preferably 80° C. to 95° C. The amount of this addition is based on the content of organically-bound chlorine in the reaction mixture. After the addition of water, the reaction mixture is desalinated via one or more cation exchangers and subsequently anion exchangers. Water is removed by distillation, and the diglycerol/polyglycerol mixture (containing a proportion of glycerol) is separated into diglycerol, higher polyglycerols and, if appropriate, glycerol by fractional distillation.

33 Claims, No Drawings

PROCESS FOR THE PREPARATION OF POLYGLYCEROLS

Background of the Invention

The present invention relates to a process for the preparation of polyglycerols (containing more than 50% by weight of diglycerol) having a low content of cyclic components, by reacting chlorohydrins.

U.S. Pat. No. 2,520,670 discloses a process for the preparation of polyglycerols in which glycerol-α-monochlorohydrin is reacted with glycerol in the presence of concentrated alkali at an elevated temperature to give a mixture of polyglycerols. This process has the disadvantage that the reaction time is relatively long, the proportion of polyglycerol is high and, after the completion of the reaction, the reaction mixture has to be worked up with lower aliphatic alcohols. The yield of polyglycerols and their content of cyclic components are not disclosed.

Summary of the Invention

It is therefore an object of the present invention to provide a process by which polyglycerols may be obtained in good yields with only a low proportion of cyclic components. In this regard it should at the same time not be necessary to isolate the intermediate products (chlorohydrin/ether mixture), or work up the end products by treatment with organic solvents.

These and other objects according to the invention are achieved by a process for the preparation of polyglycerols containing more than 50% by weight of diglycerol and having a low content of cyclic components from chlorohydrins, comprising the steps of reacting epichlorohydrin with α-monochlorohydrin in the presence of an acid or a compound with an acid reaction at a temperature of about 20° to 120° C, in a molar ratio of epichlorohydrin to α-monochlorohydrin of about 0.8:1 to 1:2.5; adding a solution having an alkaline reaction to the resulting, unseparated reaction mixture, at a temperature of about 50° C. to 120°, the amount of the addition being based on the content of organically-linked chlorine in the reaction mixture; desalinating the reaction mixture, after the addition of water, first with one or more cation exchangers and subsequently with one or more anion exchangers; removing water by distillation; and separating the reaction mixture into diglycerol, higher polyglycerols and glycerol, by fractional distillation.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Detailed Description of the Preferred Embodiments

According to the present invention, α-monochlorohydrin is reacted with epichlorohydrin at temperatures of 20° to 120° C., preferably 50° C. to 100° C., in a molar ratio of epichlorohydrin to α-monochlorohydrin of 0.8:1 to 1:2.5. The reaction occurs in the presence of acids or compounds with an acid reaction. A medium having an alkaline reaction, preferably an aqueous solution having an alkaline reaction, is added to the resulting, unseparated reaction mixture, at a temperature of 50° C. to 120° C., preferably 80° C. to 95° C. The amount of this addition is determined by the content of organically bound chlorine in the reaction mixture. The reaction mixture is then desalinated, after the addition of water, over one or more cation exchangers and subsequently anion exchangers. Water is removed by distillation and the diglycerol/polyglycerol mixture (containing a proportion of glycerol) is separated into diglycerol, higher polyglycerols and, if appropriate, glycerol, by fractional distillation.

The acid or compounds having an acid reaction may be mineral acids, Lewis acids, halogenated carboxylic acids, preferably sulfuric acid, phosphoric acid or phosphorous acid, boron trifluoride, boron trifluoride-etherate, iron-III chloride and/or tin tetrachloride, trifluoroacetic acid and/or chloroacetic acid. These are used in a concentration of about 0.1 to 2% by weight, preferably about 0.1 to 1% by weight, relative to the amount by weight of α-monochlorohydrin employed.

In an advantageous embodiment of the invention, the reaction mixture which has been reacted in an alkaline solution is diluted by the addition of water to an approximately 40–70% strength by weight solution, preferably about 50–60% by weight solution, and is desalinated at temperatures of about 30° to 80° C., preferably about 40° C. to 60° C., over a combination of strongly acid cation exchangers and subsequent weakly basic anion exchangers.

In a preferred embodiment, an alkali metal carbonate solution having an alkaline reaction, preferably a concentrated sodium carbonate solution, is added to the unseparated reaction mixture from the reaction of epichlorohydrin with α-monochlorohydrin or a higher polyglycerol.

It is preferred to mix the unseparated reaction mixture from the reaction of epichlorohydrin with α-monochlorohydrin, which contains diglycerol and, if appropriate, its higher polyglycerols, with the solution having an alkaline reaction, preferably sodium carbonate solution, under forced agitation. The unseparated reaction mixture from the reaction of epichlorohydrin with α-monochlorohydrin is preferably added to the previously charged solution having an alkaline reaction, preferably sodium carbonate solution.

It is advantageous to add the solution having an alkaline reaction, preferably sodium carbonate solution to the reaction product, in an equivalent ratio of alkali metal carbonate to the content of organically-linked chlorine of about 1:1 to 1.2:1, preferably about 1.05:1 to 1.1:1.

In a further preferred embodiment, α-monochlorohydrin and/or epichlorohydrin which is unreacted or has been employed in excess is removed by distillation, preferably vacuum distillation, after the reaction of epichlorohydrin with α-monochlorohydrin, and is recycled to the process, and the alkaline hydrolysis is carried out subsequently.

The mixture of the reaction mixture and the aqueous solution having an alkaline reaction preferably has a pH range of about 7.0 to 13, preferably about 8 to 12.

In a further preferred embodiment, the reaction mixture is cooled to room temperature after the reaction, and the bulk of the precipitated salt is removed, preferably by filtration.

The regeneration of the exchange material in the cation exchangers is carried out by means of cocurrent or composition cocurrent regeneration.

The solution containing diglycerol is advantageously passed through the ion exchangers under an excess pressure.

The solution containing diglycerol is preferably passed through one or more cation exchangers and at least one anion exchanger under a pressure of about 1.1 to 10 bar, preferably about 2 to 6 bar.

The ion exchange material of the cation exchanger and/or anion exchanger is preferably covered by a strainer plate, perforated plate or a device mounted so as to be vertically movable above the ion exchanger, which covers the exchange material and makes possible a uniform passage of liquid, and/or by an inert compression molding material and/or elastic plastic material.

It is advantageous for the cation exchange materials and anion exchange materials employed to be heat resistant up to over 80° C., preferably up to over 100° C.

The strongly acid cation exchange material and the weakly basic anion exchange material preferably have an internal surface area (measured by the BET method) of more than 25 m$^2$/g, preferably about 50 to 100 m$^2$/g.

The solution containing diglycerol is preferably passed through the ion exchangers at a flow rate of about 0.5 m/hour to 15 m/hour, preferably about 1 m/hour to 5 m/hour The invention is exemplified by means of the following illustrative embodiments:

Example 1

α-Monochlorohydrin (1.326 kg = 12 mol) and 2 ml of SnCl$_4$ are placed into a 2 l double-walled reactor (heating liquid : oil; inert gas atmosphere N$^2$) and heated to approximately 60° C.

Epichlorohydrin (1.11 kg = 12 mol) is added dropwise over the course of 2 hours at such a rate that the temperature does not exceed 80° C., the heating oil being cooled via a heat exchanger if necessary. The reaction is complete after a further hour at 70° C.

An amount (plus 10% excess) of a 2-molar sodium carbonate solution corresponding to the content of organically-linked chlorine in the reaction solution described above is heated to approximately 90° C. The crude chlorohydrin/ether mixture is metered in with stirring over the course of 2 hours. The heating is stopped after a further hour at 90° C., and the reaction mixture is neutralized by adding half-concentrated hydrochloric acid.

The neutral reaction solution is concentrated in vacuo, the precipitated salts are filtered off and the filtrate is desalinated, after dilution with water, via a combination of cation and anion exchangers. This crude polyglycerol solution is evaporated in vacuo in order to free it from water.

The product mixture had the following composition (in % by weight): glycerol 44.3, cyclic diglycerol 0.4, diglycerol 38.7, cyclic triglycerol 0.3, triglycerol 12.7, cyclic tetraglycerol 0.3, tetraglycerol 2.8, and pentaglycerol 0.5.

Example 2

α-Monochlorohydrin (1.326 kg = 12 mol) and 8 ml of phosphorous acid (30% solution in water) are placed into a 2 l double-walled reactor (heating liquid : oil) and are heated to 80° C.

Epichlorohydrin (1.11 kg = 12 mol) is added dropwise over the course of 2 hours at such a rate that the temperature does not exceed 95° C., the heating oil being cooled via a heat exchanger if necessary. The reaction is complete after a further hour at 85° C.

The hydrolysis of the reaction solution and its work up are carried out as described in Example 1.

The product mixture had the following composition (in % by weight): glycerol 46.1, cyclic diglycerol 0.6, diglycerol 40.8, cyclic triglycerol 0.6, triglycerol 9.2, cyclic tetraglycerol 0.3, tetraglycerol 2.1 and pentaglycerol 0.3.

What is claimed is:

1. A process for the preparation of polyglycerols containing more than 50% by weight of diglycerol and having a low content of cyclic components from chlorohydrins, comprising the steps of:

reacting epichlorohydrin with α-monochlorohydrin in the presence of an acid or a compound with an acid reaction at a temperature of about 20° C. to 120° C., in a molar ratio of epichlorohydrin to α-monochlorohydrin of about 0.8:1 to 1:2.5;

adding a solution having an alkaline reaction to the resulting, unseparated reaction mixture, at a temperature of about 50° C. to 120°, the amount of the addition being based on the content of organically-linked chlorine in the reaction mixture;

desalinating the reaction mixture, after the addition of water, first with one or more cation exchangers and subsequently with one or more anion exchangers;

removing water by distillation; and separating the reaction mixture into diglycerol, higher polyglycerols and glycerol, by fractional distillation.

2. The process as claimed in claim 1, wherein the acid or compound having an acid reaction is selected from the group consisting of mineral acids, Lewis acids, and halogenated carboxylic acids, in a concentration of 0.1 to 2% by weight, relative to the amount by weight of α-monochlorohydrin employed.

3. The process as claimed in claim 1, wherein the reaction mixture which has been reacted in an alkaline solution is diluted by the addition of water to a 70–40% strength by weight solution, and is desalinated at a temperature between 30° C. to 80° C., over a combination of strongly acid cation exchangers and weakly basic anion exchangers.

4. The process as claimed in claim 1, wherein an alkali metal carbonate solution having an alkaline reaction is added to the unseparated reaction mixture from the reaction of epichlorohydrin with α-monochlorohydrin.

5. The process as claimed in claim 1, wherein the unseparated reaction mixture from the reaction of epichlorohydrin with α-monochlorohydrin is mixed with the solution having an alkaline reaction under forced agitation.

6. The process as claimed in claim 1, wherein the solution having an alkaline reaction is added to the reaction product of epichlorohydrin with α-monochlorohydrin in an equivalent or molar ratio of alkali metal carbonate of 1:1 to 1.2:1, relative to the content of organically-bound chlorine.

7. The process as claimed in claim 1, wherein unreacted α-monochlorohydrin and epichlorohydrin are removed by distillation after the reaction of epichlorohydrin with α-monochlorohydrin and recycled to the process, and the alkaline hydrolysis is carried out subsequently.

8. The process as claimed in claim 1, wherein the mixture of the reaction mixture and the aqueous solution having an alkaline reaction exhibits a pH range of 7.0 to 13.

9. The process as claimed in claim 1, wherein the reaction mixture is cooled to room temperature after the reaction, and precipitated salt is removed.

10. The process as claimed in claim 1, wherein regeneration of cation exchange material in the cation exchangers is effected by means of cocurrent or composite cocurrent regeneration.

11. The process as claimed in claim 1, wherein the solution to be desalinated is passed through the ion exchangers under an excess pressure.

12. The process as claimed in claim 1, wherein the solution to be desalinated is passed through one or more cation exchangers and at least one anion exchanger under a pressure of 1.1-10 bar.

13. The process as claimed in claim 1, wherein the ion exchange material of the exchangers is covered by a strainer plate, perforated plate, a device mounted so as to be vertically movable above the ion exchanger, which covers the exchange material and produces a uniform passage of liquid, an inert compression molding material, or an elastic plastic material.

14. The process as claimed in claim 1, wherein the cation exchange materials and anion exchange materials employed are resistant to heat up to over 80° C.

15. The process as claimed in claim 1, wherein the strongly acid cation exchange material and the weakly basic anion exchange material have an internal surface area, as measured by the BET method, of more than 25 $m^2/g$.

16. The process as claimed in claim 1, wherein the solution to be desalinated is passed through the ion exchanger at a flow rate of 0.5 m/hour to 15 m/hour.

17. The process as claimed in claim 1, wherein the epichlorohydrin is reacted with the α-monochlorohydrin at a temperature in the range of about 50° C. to 100° C.

18. The process as claimed in claim 1, wherein the adding step takes place at a temperature in the range of about 80° C. to 95° C.

19. The process as claimed in claim wherein the solution having an alkaline reaction is an aqueous solution.

20. The process as claimed in claim 2, wherein the acid or compound having an acid reaction is sulfuric acid, phosphoric acid or phosphorous acid, boron trifluoride, boron trifluoride-etherate, iron-III chloride and-/or tin tetrachloride, trifluoroacetic acid or chloroacetic acid.

21. The process as claimed in claim 2, wherein the amount of acid or compound having an acid reaction is present in a concentration of 0.1 to 1% by weight, relative to the amount by weight of α-monochlorohydrin employed.

22. The process as claimed in claim 1, wherein the reaction mixture which has been reacted in an alkaline solution is diluted by the addition of water to a 60–50% strength by weight solution.

23. The process as claimed in claim 1, wherein the desalination is performed at a temperature between 40° C. to 60° C.

24. The process as claimed in claim 4, wherein the alkali metal carbonate solution having an alkaline reaction is a concentrated sodium carbonate solution.

25. The process as claimed in claim 5, wherein the unseparated reaction mixture from the reaction of epichlorohydrin with α-monochlorohydrin is added to the solution having an alkaline reaction.

26. The process as claimed in claim 6, wherein the solution having an alkaline reaction is added to the reaction product of epichlorohydrin with α-monochlorohydrin in an equivalent or molar ratio of alkali metal carbonate of 1.05:1 to 1.1:1, relative to the content of organically-bound chlorine.

27. The process as claimed in claim 7, wherein unreacted α-monochlorohydrin and epichlorohydrin are removed by vacuum distillation.

28. The process as claimed in claim 8, wherein the mixture of the reaction mixture and the solution having an alkaline reaction exhibits a pH range of 8 to 12.

29. The process as claimed in claim 9, wherein the precipitated salt is removed by filtration.

30. The process as claimed in claim 12, wherein the solution to be desalinated is passed through one or more cation exchangers and at least one anion exchanger under a pressure of 2-6 bar.

31. The process as claimed in claim 1, wherein the cation exchange materials and anion exchange materials employed are resistant to heat up to over 100° C.

32. The process as claimed in claim 15, wherein the strongly acid cation exchange material and the weakly basic anion exchange material have an internal surface area, as measured by the BET method, of about 50 to 100 $m^2/g$.

33. The process as claimed in claim 16, wherein the solution to be desalinated is passed through the ion exchanger at a flow rate of 1 m/hour to 5 m/hour.

* * * * *